US009040564B2

(12) United States Patent
Ukai et al.

(10) Patent No.: US 9,040,564 B2
(45) Date of Patent: May 26, 2015

(54) STABILIZED COMPOSITION

(75) Inventors: Koji Ukai, Kakamigahara (JP);
Norishige Takami, Kakamigahara (JP)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 1224 days.

(21) Appl. No.: 11/937,393

(22) Filed: Nov. 8, 2007

(65) Prior Publication Data
US 2008/0145421 A1 Jun. 19, 2008

Related U.S. Application Data

(63) Continuation-in-part of application No. 11/919,229, filed as application No. PCT/JP2006/308065 on Apr. 17, 2006, now abandoned.

(30) Foreign Application Priority Data

Apr. 28, 2005 (JP) ................. 2005-130695

(51) Int. Cl.
A61K 31/4439 (2006.01)
A61K 31/4184 (2006.01)
A61K 9/50 (2006.01)

(52) U.S. Cl.
CPC ........... *A61K 31/4184* (2013.01); *A61K 9/5047* (2013.01); *A61K 9/5078* (2013.01); *A61K 31/4439* (2013.01)

(58) Field of Classification Search
CPC ..................... A61K 31/4439; A61K 47/38
See application file for complete search history.

(56) References Cited

U.S. PATENT DOCUMENTS

| 4,808,596 | A | 2/1989 | Matsuishi et al. | |
|---|---|---|---|---|
| 5,039,806 | A | 8/1991 | Brandstram et al. | |
| 5,045,321 | A | 9/1991 | Makino et al. | |
| 5,430,042 | A | 7/1995 | Lindberg et al. | |
| 6,379,705 | B1 * | 4/2002 | Mendes et al. | 424/490 |
| 2002/0064555 | A1 | 5/2002 | Cullen et al. | |
| 2004/0266828 | A1 | 12/2004 | Garvey et al. | |
| 2005/0003005 | A1 | 1/2005 | Shimizu et al. | |
| 2005/0042277 | A1 * | 2/2005 | Srinivas et al. | 424/452 |
| 2006/0159760 | A1 * | 7/2006 | Yoneyama et al. | 424/472 |
| 2006/0165793 | A1 * | 7/2006 | Ukai | 424/470 |

FOREIGN PATENT DOCUMENTS

| AU | 200013541 A1 | 9/2000 |
|---|---|---|
| EP | 0 187 977 A1 | 7/1986 |
| EP | 0 244 380 A2 | 11/1987 |
| EP | 0 254 588 A1 | 1/1988 |
| EP | 0277741 A1 | 8/1988 |
| EP | 1 072 257 | 1/2001 |
| EP | 1 086 694 | 3/2001 |
| EP | 1 105 387 B1 | 6/2001 |
| EP | 1 652 514 A1 | 5/2006 |
| JP | 59-181277 A | 10/1984 |
| JP | 62-207271 A | 9/1987 |
| JP | 62-258316 A | 11/1987 |
| JP | 62-277322 A | 12/1987 |
| JP | 63-146882 A | 6/1988 |
| JP | 01-190682 A | 7/1989 |
| JP | 02-022273 A | 1/1990 |
| JP | 5-92918 A | 4/1993 |
| JP | 5-112559 A | 5/1993 |
| JP | 05-117268 A | 5/1993 |
| JP | 5-262763 A | 10/1993 |
| JP | 05-507713 A | 11/1993 |
| JP | 2000-212085 A | 8/2000 |
| JP | 2001-199878 A | 7/2001 |
| JP | 2003-137771 A | 5/2003 |
| JP | 2003-192579 A | 7/2003 |
| JP | 2004-292442 A | 10/2004 |
| WO | WO 91/19711 A1 | 12/1991 |
| WO | WO-91/19712 A1 | 12/1991 |
| WO | WO-99/53905 A1 | 10/1999 |
| WO | WO-00/50037 A1 | 8/2000 |
| WO | WO-03/032953 A1 | 4/2003 |
| WO | WO-2004/035020 A2 | 4/2004 |
| WO | WO 2004/035090 | 4/2004 |
| WO | WO 2004/066924 | 8/2004 |
| WO | WO2004/080439 * | 9/2004 |
| WO | WO-2004/080439 A1 | 9/2004 |

(Continued)

OTHER PUBLICATIONS

Williams et al. (Aliment Pharmacol Ther 1999, 13 (Suppl. 3), 3-10), Review article: the pharmacology of rabeprazole.*
The Oxford English Dictionary definition of granule (accessed Jun. 2014).*
Office Action issued Jan. 12, 2011 in Indian Patent Application No. 8176/DELNP/2007.
Arthur H. Kibbe, "Handbook of Pharmaceutical Excipients", American Pharmaceutical Association and Pharmaceutical Press, London, 2000, p. 195, paragraph 6, XP-002562768.
Arthur H. Kibbe, "Handbook of Pharmaceutical Excipients", American Pharmaceutical Association and Pharmaceutical Press, London, 2000, p. 244, paragraph 6, XP-002562910.
Arthur H. Kibbe, "Handbook of Pharmaceutical Excipients", American Pharmaceutical Association and Pharmaceutical Press, London, 2000, p. 252, paragraph 6, XP-002562769.

(Continued)

*Primary Examiner* — Tigabu Kassa
(74) *Attorney, Agent, or Firm* — Birch, Stewart, Kolasch & Birch, LLP

(57) ABSTRACT

It is intended to provide a pharmaceutical composition which contains a proton pump inhibitor and is stable even if it is stored for a long time. It is also intended to provide a pharmaceutical composition which contains a proton pump inhibitor susceptible to acid, and does not dissolve in the stomach but dissolves in the intestine to release a primary drug product promptly. The object could be achieved by the pharmaceutical composition characterized in that a layer containing a proton pump inhibitor and ethyl cellulose, a layer containing an enteric polymer, and if necessary an intermediate layer composed of one or more layers are formed on a pharmacologically inactive core substance. The intermediate layer is composed of a water-insoluble polymer, a water-soluble polymer, a lubricant and the like.

13 Claims, 1 Drawing Sheet

(56) References Cited

FOREIGN PATENT DOCUMENTS

| WO | WO-2005/011637 A1 | | 2/2005 |
|---|---|---|---|
| WO | WO 2005011637 | * | 2/2005 |

OTHER PUBLICATIONS

Arthur H. Kibbe, "Handbook of Pharmaceutical Excipients", American Pharmaceutical Association and Pharmaceutical Press, London, 2000, p. 424, paragraph 6, XP-002562911.
European Search Report, EP 06 73 1994, Jan. 29, 2010, pp. 1-7.
N. Matsuishi et al. II, "Preparation of imidazo [4,5-b]pyridines as antiulcer agents and their pharmaceutical compositions," English translation of Abstract of JP 01190682-A2 published Jul. 31, 1989, Accession No. 1990:77192 CAPLUS.
N.J.V. Bell et al., "Appropriate Acid Suppression for the Management of Gastro-Oesophageal Reflux Disease," Digestion 1992, 51(supp 1): 59-67, S. Karger Medical and Scientific Publishers.
S. R. Vippagunta et al., "Crystalline Solids," Advanced Drug Delivery Reviews, 48 (2001), 3-26, Elsevier Science B.V.
J. K. Guiillory, "Generation of Polymorphs, Hydrates, Solvates, and Amorphous Solids," in Brittain (ed.), Polymorphism in Pharmaceutical Solids, 95, Marcel Dekker, NY 1999, 183-226.
English translation of Office Action issued Jul. 30, 2012, in Korean Patent Application No. 10-2007-7023561.
Notice to Submit a Response issued Sep. 20, 2012, in Korean Patent Application No. 10-2007-7027320, with English translation.
Notice of Allowance issued Jul. 29, 2013, in Korean Patent Application No. 10-2007-7027320, with partial English translation.
Response filed Oct. 31, 2012, in reply to the Notification of Defects issued Apr. 8, 2010, in Israeli Patent Application No. 186778, with English translation.
Notification Before Examining Israeli Patent Application No. 186778, issued Feb. 9, 2009, with English translation.
Notification of Defects dated Apr. 8, 2010, issued in Israeli Patent Application No. 186778, with English translation.
Response dated Jun. 8, 2009, filed in reply to the Notification Before Examining Israeli Patent Application No. 186778 issued Feb. 9, 2009, with English translation.
Office Action issued Feb. 10, 2012, in Japanese Patent Application No. 2007-514590.
Reply filed Sep. 22, 2013, in response to the Office Action issued Jun. 2, 2013, in Israeli Patent Application No. 186778, with English translation.
Office Action issued Jul. 30, 2012, in Korean Patent Application No. 10-2007-7023561.
English translation of Amendment filed Mar. 20, 2013, in Korean Patent Application No. 10-2007-7027320.
Examiner's First Report Issued Nov. 22, 2011, in Australian Patent Application No. 2006242067.
Extended European Search Report issued Jan. 29, 2010, in European Patent Application No. 06731994.7.
Office Action issued Feb. 12, 2010, in Chinese Patent Application No. 200680022749, with English translation.
Office Action issued Jan. 12, 2011, in Indian Patent Application No. 8176/DELNP/2007.
Response dated Jun. 20, 2011, filed in reply to Office Action issued Jan. 12, 2011, in Indian Patent Application No. 8176/DELNP/2007.
Reponse dated Jun. 24, 2010, filed in reply to Office Action issued Feb. 12, 2011, in Chinese Patent Application No. 200680022749, with English translation.
Response filed Oct. 18, 2010, in reply to Extended European Search Report issued Jan. 29, 2010, in European Patent Application No. 06731994.7.
English translation of JP 5-112559-A dated May 7, 1993.
English translation of JP 5-262763-A dated Oct. 12, 1993.
English translation of Office Action mailed Feb. 10, 2012, in Japanese Patent Application No. 2007-514590.
Response filed Feb. 24, 2012, in reply to the Examiner's First Report issued Nov. 22, 2011, in Australian Patent Application No. 2006242067.
Office Action issued May 3, 2012, in Canadian Patent Application No. 2,605,839.
Response filed Apr. 10, 2012, in reply to the Office Action issued Feb. 7, 2012, in Japanese Patent Application No. 2007-514590, with English translation.

* cited by examiner

STABILIZED COMPOSITION

CROSS-REFERENCE TO RELATED APPLICATIONS

This application is a continuation-in-part of an international application PCT/JP2006/308065 filed on Apr. 17, 2006 and having US as one of the designated countries, the content of which is herein incorporated by reference.

BACKGROUND OF THE INVENTION (1) Field of the Invention

The present invention relates to a novel pharmaceutical composition. More specifically, the present invention relates to a stable solid pharmaceutical composition comprising a benzimidazole compound.

(2) Description of Related Art

Some benzimidazole compounds have a proton pump inhibitory action, and are widely employed as a therapeutic drug for gastric ulcers, reflux esophagitis, duodenal ulcers, anastomotic ulcers, Zollinger-Ellison syndrome and the like. It is thought that proton pump inhibitors exhibit the above-described pharmacological action by inhibiting the activity of the proton pump located at the final stage of the gastric acid secretion mechanism in the parietal cells of the gastric mucosa.

However, some benzimidazole compounds are unstable against acid or water and are susceptible to decomposing. Accordingly, a pharmaceutical composition which contains such a benzimidazole compound may decompose during storage from the action of an acidic substance in the drug product formulation or may decompose from gastric acid when taken internally in the stomach, whereby the desired pharmacological activity cannot be obtained.

Therefore, when producing a pharmaceutical composition which contains the above-described benzimidazole compound, it is necessary to take special measures, such as ensuring the compound does not come into contact with an acidic substance, blending with an alkaline substance or making into an enteric formulation in which the drug does not dissolve in the stomach.

Various investigations have been carried out for the purpose of stabilizing such unstable benzimidazole compounds. Related art documents which illustrate the investigative results include the following.

For example, JP-A-62-277322 describes a pharmaceutical composition composed of a basic inorganic salt of magnesium and/or calcium blended in a benzimidazole or derivative thereof having antiulcer activity. Further, JP-A-62-258316 describes an oral pharmaceutical drug product formulation comprising an acid-unstable compound such as omeprazole, wherein the drug product formulation contains a core containing an acid-unstable compound and an alkali-reactive compound, an intermediate layer containing a tablet excipient which is soluble in water or rapidly decomposable in water or a water-soluble film-forming compound which is a polymer, and an enteric coating.

JP-A-2003-192579 describes granules comprising a principal ingredient layer containing an acid-unstable medicament such as proton pump inhibitor in an amount of about 12% by weight or more based on the total amount, an intermediate coating layer formed on the principal ingredient layer, and an enteric coating formed on the intermediate coating layer, wherein the granules contain a basic inorganic salt and have an average particle size of about 600 μm or more.

JP-A-2001-199873 describes a sustained-release pellet comprising: (a) an inert core; (b) an active layer disposed over the inert core, formed from a benzimidazole compound, an inert, non-basic polymer soluble in water and one or more pharmaceutically acceptable inert excipients; (c1) an intermediate layer which is formed from an inert, non-basic polymer soluble in water and one or more pharmaceutically acceptable inert excipients; (c2) an intermediate layer having a system of modified release which comprises an inert, non-basic polymer soluble in water and a non-basic polymer insoluble in water; and (d) an exterior layer comprising an enteric coating.

WO 2005/011637 describes a pharmaceutical composition characterized by having, on a core substance, a layer (1) containing crospovidone, a layer (2) containing sodium hydroxide which is adjacent to the layer containing crospovidone, and a layer (3) containing a benzimidazole compound or a pharmacologically acceptable salt thereof which is adjacent to the layer containing sodium hydroxide.

SUMMARY OF THE INVENTION

However, with the techniques described in these documents, it is necessary to blend a basic substance in order to ensure the stability of the benzimidazole compound. For example, in the techniques described in JP-A-62-277322, JP-A-62-258316, JP-A-2003-192579 and WO 2005/011637, in addition to the benzimidazole compound, a basic substance is also blended, and decomposition progresses unless the basic substance is blended in. The technique described in JP-A-2001-199878 relates to a so-called sustained-release agent used when to slow down dissolution of the drug, meaning that quick-acting properties cannot be expected.

Therefore, there is a need to realize as soon as possible a heretofore-unknown pharmaceutical composition which is not blended with a basic substance, which is stable against acidic substances blended in a drug product formulation or gastric acid and which can quickly release the benzimidazole compound after reaching the intestine.

In view of these circumstances, and as a result of intensive investigation to resolve the above-described problems, the present inventors discovered that such problems could be unexpectedly resolved by blending ethyl cellulose, which is insoluble in water, and which is normally used for delaying dissolution of the drug, in the same coating layer as the above-described benzimidazole compound, thereby arriving at the present invention.

Specifically, the present invention is:
(1) A pharmaceutical composition characterized that a core substance is coated with a principal ingredient layer comprising a benzimidazole compound and ethyl cellulose.

The present invention also includes the following aspects.
(2) The pharmaceutical composition according to the above-described (1), characterized that the pharmaceutical composition is further coated with an exterior layer comprising an enteric polymer on an exterior side of the principal ingredient layer.
(3) The pharmaceutical composition according to the above-described (2), wherein the enteric polymer is one or more selected from the group consisting of hydroxypropylmethyl cellulose phthalate, hydroxypropylmethyl cellulose acetate succinate, methacrylic acid methacrylic acid methyl copolymer, methacrylic acid acrylic acid ethyl copolymer, carboxymethylethyl cellulose and cellulose acetate phthalate.

(4) The pharmaceutical composition according to the above-described (2) or (3), wherein one or more intermediate layers is coated between the principal ingredient layer and the exterior layer.
(5) The pharmaceutical composition according to the above-described (4), wherein two intermediate layers are coated.
(6) The pharmaceutical composition according to the above-described (4) or (5), wherein the intermediate layer comprises one or more selected from the group consisting of a non-water-soluble polymer, a water-soluble polymer and a lubricant.
(7) The pharmaceutical composition according to any one of the above-described (4) to (6), wherein the intermediate layer comprises a first layer comprising a non-water-soluble polymer, a water-soluble polymer and a lubricant, and a second layer comprising crospovidone.
(8) The pharmaceutical composition according to any one of the above-described (1) to (7), wherein based on the total amount of the layer comprising the benzimidazole compound and ethyl cellulose the weight of ethyl cellulose in said layer is not more than 25%.
(9) The pharmaceutical composition according to any one of the above-described (1) to (8), wherein the benzimidazole compound is a proton pump inhibitor.
(10) The pharmaceutical composition according to the above-described (9), wherein the proton pump inhibitor is one or more selected from the group consisting of rabeprazole, omeprazole, pantoprazole, lansoprazole, nepaprazole, leminoprazole, esomeprazole, 2-[[[4-(2,2-dimethyl-1,3-dioxan-5-yl)methoxy-3,5-dimethylpyridin-2-yl]methyl]sulfinyl]-1H-benzimidazole and pharmaceutically acceptable salts thereof.
(11) The pharmaceutical composition according to the above-described (9) or (10), wherein the proton pump inhibitor is rabeprazole, 2-[[[4-(2,2-dimethyl-1,3-dioxan-5-yl)methoxy-3,5-dimethylpyridin-2-yl]methyl]sulfinyl]-1H-benzimidazole or a pharmaceutically acceptable salt thereof.
(12) The pharmaceutical composition according to any one of the above-described (1) to (11), wherein the core substance is a granule substance having 1 or more components selected from the group consisting of sugars, sugar alcohols, celluloses and starches.
(13) The pharmaceutical composition according to any one of the above-described (1) to (12), which is a granule.
(14) The pharmaceutical composition according to any one of the above-described (1) to (12), which is a tablet or an encapsulated formulation.
(15) The pharmaceutical composition according to the above-described (13), which is a drug product formulation used for tube administration further comprising a thickening agent.
(16) The pharmaceutical composition according to any one of the above-described (2) to (15), characterized in that in a dissolution test using a test solution having a pH of 5.5 or higher, 75% or more of the benzimidazole compound or proton pump inhibitor is dissolved within 30 minutes.
(17) The pharmaceutical composition according to any of the above-described (1) to (16), which is a treatment or prophylactic drug for a disorder or symptoms caused by gastric acid.
(18) The pharmaceutical composition according to the above-described (17), wherein the disorder or symptoms caused by gastric acid is gastric ulcer, duodenal ulcer, anastomotic ulcer, reflux esophagitis, Zollinger-Ellison syndrome, symptomatic reflux esophagitis, endoscopy-negative reflux esophagitis, nonerosive reflux esophagitis, gastroesophageal reflux disease, NUD (non-ulcer dyspepsia), pharyngolarynx anomaly, Barrett's esophagus, NSAID-induced ulcer, gastritis, gastric bleeding, hemorrhagic gastritis, digestive tract bleeding, peptic ulcer, hemorrhagic ulcer, stress ulcer, gastric hyperacidity, dyspepsia, gastroparesis, aged person ulcer, intractable ulcer, acute gastric mucosal lesion, pyrosis, pyrosis during sleep apnea syndrome, bruxism, stomachache, heavy stomach, retching, nausea, temporomandibular joint disorder or gastric erosion.
(19) The pharmaceutical composition according to the above-described (17), wherein the disorder or symptoms caused by gastric acid is gastric ulcer, duodenal ulcer, anastomotic ulcer, reflux esophagitis, Zollinger-Ellison syndrome, symptomatic reflux esophagitis, endoscopy-negative reflux esophagitis, nonerosive reflux esophagitis or acute gastric mucosal lesion.
(20) The pharmaceutical composition according to the above-described (17), wherein the disorder or symptoms caused by gastric acid is reflux esophagitis or symptomatic reflux esophagitis.
(21) The pharmaceutical composition according to the above-described (17), wherein the disorder caused by gastric acid is gastric ulcer or duodenal ulcer.
(22) The pharmaceutical composition according to any of the above-described (1) to (16), which is a bacteria eliminating agent or a bacteria eliminating auxiliary agent for gastric *Helicobacter pylori*.

The pharmaceutical composition according to the present invention can effectively stop decomposition of the benzimidazole compound. Further, when taken internally, dissolution of the benzimidazole compound in the stomach can be prevented, thereby allowing decomposition of the benzimidazole compound by gastric acid to be stopped. In addition, when the pharmaceutical composition reaches the intestines, the drug rapidly dissolves, thereby allowing the duration until the drug takes effect to be shortened. With the pharmaceutical composition according to the present invention, a granule formulation can be obtained which is easy even for children to take. Since this granule formulation can be dispersed in water or the like, using a cannula it can even be given to infants who are unable to take the drug product by themselves.

Further, the obtained granule formulation can be made into various dosage forms, such as tablets formed by tableting or encapsulated formulations formed by filling into capsules.

DETAILED DESCRIPTION OF THE INVENTION

Figure 1:
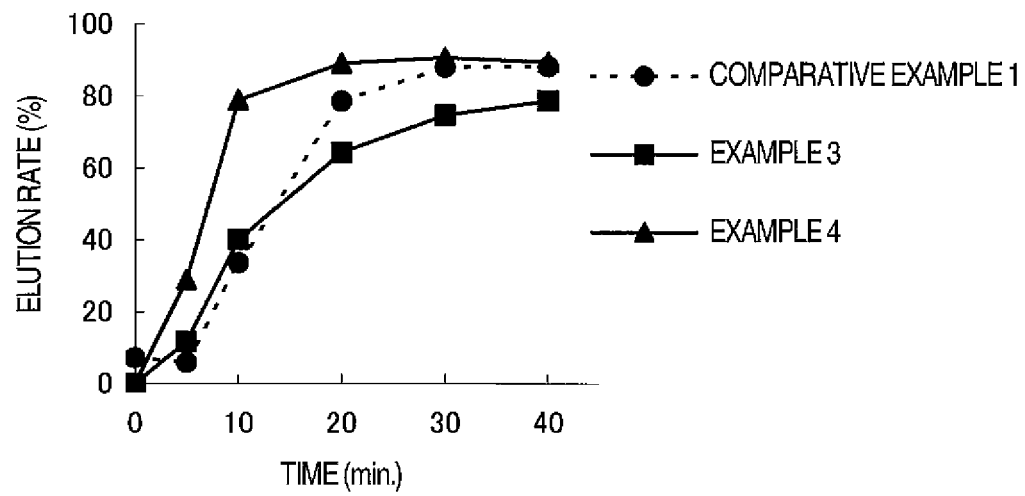
FIG. 1 is a graph showing the results of the dissolution test of the granule formulations according to the present invention.

In the present invention the benzimidazole compound is not especially limited, and a preferable example may include a proton pump inhibitor.

Examples of such a proton pump inhibitor include rabeprazole, omeprazole, pantoprazole, lansoprazole, nepaprazole, leminoprazole, esomeprazole and 2-[[[4-(2,2-dimethyl-1,3-dioxan-5-yl)methoxy-3,5-dimethylpyridin-2-yl]methyl]sulfinyl]-1H-benzimidazole sodium salt. Further preferable examples include pharmaceutically acceptable salts of these compounds, such as the sodium, potassium, magnesium and calcium salts or hydrates thereof. Preferable are rabeprazole and 2-[[[4-(2,2-dimethyl-1,3-dioxan-5-yl)methoxy-3,5-dimethylpyridin-2-yl]methyl]sulfinyl]-1H-benzimidazole or pharmaceutically acceptable salts thereof.

In the present invention, the core substance (hereinafter, sometimes referred to as "seed") is a substance which acts as a core for forming a granule shape by adsorbing the medicinal component, additives and the like onto the core surface in layers. The components of the seed are not especially limited, although it is preferred to use substances which essentially do not react with the other components in the pharmaceutical composition, like a sugar component such as sucrose or lactose, a sugar alcohol such as mannitol or erythritol, cellulose such as crystalline cellulose, or starch such as cornstarch or potato starch. The expression "essentially do not react" means not having an adverse impact on the stability of the benzimidazole compound. Commercially available spherical granules or spherical granules prepared by mixing one or more of the above-described components, granulating the mixture and sizing the resultant granules can be used as the seeds. In addition, seeds prepared by freely mixing and granulating various additives into one or more selected from the group consisting of sugars, sugar alcohols, celluloses and starches may also be used.

The shape of the seeds is not especially limited, although preferably the seeds have a shape with a large surface area, such as a sphere, a Spheroid or a rugby ball shape, which has excellent flowability. For a spherical shape, the average particle size is usually about 80 to 2,000 µm, preferably 100 to 800 µm, and more preferably 100 to 500 µm. Commercially available seeds which can be easily obtained include Nonpareil 101, Nonpareil 103, Nonpareil 105, Nonpareil 108 (all from Freund Corporation), and Celphere (Asahi Kasei Corporation).

With the pharmaceutical composition according to the present invention, by blending ethyl cellulose in the same layer as the benzimidazole compound, the stability of the benzimidazole compound is improved, which allows effective prevention of decomposition. This layer is formed by coating or spraying onto the above-described core substance a coating solution which contains a benzimidazole compound and ethyl cellulose.

The blended amount of ethyl cellulose is 1 to 30%, and preferably 5 to 25%, based on the total amount of solid matter dissolved or dispersed in the coating solution when forming the layer. If the blended amount exceeds 30%, dissolution of the benzimidazole compound in the intestines is delayed, which is not desirable.

The solvent used when producing the coating solution may be, for example, water, ethanol, hydrous ethanol, isopropyl alcohol, acetone or the like. Preferably, the solvent is water, ethanol or hydrous ethanol.

Since the pharmaceutical composition according to the present invention contains a benzimidazole compound, as an essential component, which decomposes by an acid or water, it is preferable to coat the exterior side of the layer containing the benzimidazole compound with an enteric polymer so that it does not dissolve in the stomach. While such an enteric polymer is not limited, examples include hydroxypropylmethyl cellulose phthalate (Trade names: HP-55, HP-55S and HP-50, Shin-Etsu Chemical Co., Ltd.), hydroxypropylmethyl cellulose acetate succinate (Trade name: Shin-Etsu AQOAT, Shin-Etsu Chemical Co., Ltd.), methacrylic acid methacrylic acid methyl copolymer (Trade name: Eudragit L100, Eudragit L500-55, Eudragit S100, Rohm Pharma), methacrylic acid acrylic acid ethyl copolymer (Trade name: Eudragit L-30 D55, Rohm Pharma), carboxymethylethyl cellulose (Trade name: CMEC, Freund Corporation), polyvinyl alcohol acetate phthalate (Trade name: Opa-dry Enteric, Colorcon, Inc.) and cellulose acetate phthalate (Trade name: CAP, Wako Pure Chemical Industries, Ltd.).

The solvent used when producing the enteric coating solution may be, for example, water, ethanol, hydrous ethanol, isopropyl alcohol, acetone or the like. Preferably, the solvent is water, ethanol or hydrous ethanol. Further, the amount of solid matter dissolved or dispersed in the coating solution is usually 1 to 30% by weight, and preferably 5 to 20% by weight.

Further, the above coating solution may include a basic substance. Examples of such a basic substance include, potassium hydroxide, sodium hydroxide, magnesium hydroxide, magnesium oxide, calcium oxide, potassium carbonate, sodium carbonate, magnesium carbonate, magnesium aluminate, magnesium aluminosilicate, sodium phosphate, sodium citrate, aluminum hydroxide and calcium hydroxide.

The blended amount of a basic substance is 1 to 500% by weight, preferably 10 to 200% by weight, more preferably 12.5 to 60% by weight based on the total amount of the benzimidazole compound dissolved or dispersed in the coating solution.

In the present invention, when carrying out the enteric coating, in view of the objective of such step, the layer containing the benzimidazole compound and ethyl cellulose (hereinafter, sometimes referred to as "principal ingredient layer") is formed on the surface of the core substance, and then the enteric coating layer (hereinafter, sometimes referred to as "exterior layer") is formed on the exterior side thereof.

Further, the pharmaceutical composition according to the present invention may be provided with one or more inert intermediate layers between the principal ingredient layer containing the benzimidazole compound and ethyl cellulose and the exterior layer containing the enteric polymer. The term "inert intermediate layer" means a layer which does not adversely impact the stability of the benzimidazole compound. This intermediate layer may optionally comprise a non-water-soluble polymer, a water-decomposable or water-dispersible substance, a water-soluble polymer, a lubricant or the like. As a result of this intermediate layer, the stability of the benzimidazole compound can be improved even further, because contact with the enteric polymer, which is an acidic substance, can be prevented.

Examples of the non-water-soluble polymer and water-dispersible substance that may be contained in the intermediate layer include ethyl cellulose (Trade name: Ethocel, The Dow Chemical Company), cellulose acetate (Eastman Chemical Company), carboxymethylethyl cellulose (Trade name: CMEC, Freund Corporation), aminoalkyl methacrylate copolymer RS (Trade name: Eudragit RS, Rohm Pharma), crospovidone (Trade name: Kollidon CL, BASF AG), wax, shellac (The Japan Shellac Industries Ltd.), vinyl acetate resin, polyvinyl acetal diethylamino acetate (Trade name: AEA, Sankyo Co., Ltd.), acrylic acid ethylmethacrylic acid methyl copolymer (Trade name: Eudragit NE, Rohm Pharma), carboxymethyl cellulose (Trade name: Carmellose, Nichirin Chemical Industries, Ltd.), low-substituted hydroxypropyl cellulose (Trade name: L-HPC, Shin-Etsu Chemical Co., Ltd.) and crystalline cellulose (Trade names: Avicel, Ceolus, Asahi Kasei Corporation).

Further, examples of the water-soluble polymer and water-decomposable substance that may be contained in the intermediate layer include hydroxypropyl cellulose (Shin-Etsu Chemical Co., Ltd., Nippon Soda Co., Ltd.), hydroxypropyl methylcellulose (Trade name: TC-5, Shin-Etsu Chemical Co., Ltd.), methyl cellulose (Trade name: Metolose, Shin-Etsu Chemical Co., Ltd.), ethyl cellulose (Trade name: Ethocel, The Dow Chemical Company), carboxymethyl cellulose sodium (Trade name: Serogen, Dai-ichi Kogyo Seiyaku Co., Ltd.), carboxymethyl cellulose calcium (Trade name: Carmellose Calcium, Nichirin Chemical Industries, Ltd.), carboxymethyl starch sodium (Trade name: Explotab, Kimura Sangyo Co., Ltd.), croscarmellose sodium (Kiccolate ND-200, Nichirin Chemical Industries, Ltd.), polyvinyl alcohol (Trade name: Gohsenol, Nippon Synthetic Chemical Industry Co., Ltd.), copolyvidone (Trade name: Kollidon VA64, BASF AG; Plasdone S-630, ISP Japan Ltd.), polyvinylpyrrolidone (Trade name: Kollidon, BASF AG; Plasdone, ISP Japan Ltd.) and polyvinyl alcohol-polyethylene glycol graft copolymer (Trade name: Kollicoat IR, BASF AG).

Examples of the above-described lubricant which may be blended in the intermediate layer include magnesium stearate, calcium stearate, sodium stearyl fumarate, talc, synthetic magnesium silicate, carnauba wax, hydrogenated oil and microcrystalline wax.

Further, the intermediate layer containing one or more of the non-water-soluble polymer, water-decomposable or water-dispersible, water-soluble polymer or lubricant may be divided up into two or more layers. Such intermediate layers may be formed by preparing one or more coating solutions containing the same or different components and laminating two or more layers. For example, a first intermediate layer may be provided which contains a non-water-soluble polymer, a water-soluble polymer, and optionally, a lubricant such as magnesium stearate, and a second intermediate layer may be provided which contains a non-water-soluble polymer such as crospovidone. Especially when the benzimidazole compound is a substance that is susceptible to oxidation, it is preferable to provide two or more intermediate layers.

The solvent used when producing the above-described intermediate layer coating solution may be, for example, water, ethanol, hydrous ethanol, isopropyl alcohol, acetone or the like. Preferably, the solvent is water, ethanol or hydrous ethanol. Further, the amount of solid matter dissolved or dispersed in the coating solution is usually 1 to 30% by weight, and preferably 5 to 20% by weight.

If the pharmaceutical composition according to the present invention is subjected to a dissolution test using a test solution having a pH of 5.5 or higher, and preferably 6.5 or higher, it is preferable that 75% or more of the benzimidazole compound dissolves within 30 minutes.

The dosage form of the pharmaceutical composition according to the present invention is not especially limited, and may be, for example, as a granule formulation or fine powder formulation.
Tablets or encapsulated formulations can be produced by tableting and filling the granule formulation or fine powder formulation. The pharmaceutical composition according to the present invention is preferably a granule formulation or fine powder formulation.

The drug product formulation may also be formed by blending the granules according to the present invention with a thickening agent. The powdered granules are dispersed in water or the like when taking the drug product, and the resultant solution is administered orally or via a tube such as a nasal cannula (tube). As a result of this tube administration, the pharmaceutical composition according to the present invention can reliably be given even to infants, disabled persons or the elderly, who are unable to take the pharmaceutical composition by themselves.

Examples of the above-described thickening agent include methyl cellulose (Trade name: Metolose SM, Shin-Etsu Chemical Co., Ltd.), propylene glycol alginate ester (Trade name: Kimiloid, Kimica Corporation), xanthan gum (Trade name: Echo gum, Dainippon Pharmaceutical Co., Ltd.), purified gelatin (Trade name: Purified Gelatin, Miyagi Chemical Industrial Co., Ltd.), hydroxypropyl cellulose, hydroxypropylmethyl cellulose, polyvinyl alcohol, polyvinylpyrrolidone, carboxymethyl cellulose sodium, polyethylene glycol (Trade name: Macrogol, NOF Corporation). Preferred is propylene glycol alginate ester or methyl cellulose.

When forming the pharmaceutical composition according to the present invention as granules or a fine powder, the particle size is usually 50 to 5,000 μm, preferably 100 to 2,000 μm, and more preferably 200 to 800 μm. If the pharmaceutical composition is a granule formulation used for tube administration, the particle size is preferably small, about 50 to 500 μm. If the pharmaceutical composition is filled into capsules, the particle size may exceed 2,000 μm.

The pharmaceutical composition according to the present invention can be produced in the following manner, for example.

The benzimidazole compound and ethyl cellulose are dissolved or dispersed in ethanol or purified water to prepare a first coating solution.

The coating solution is sprayed onto a pharmacologically inert core substance, and then dried to obtain the granules according to the present invention.

Further, an enteric polymer may be dissolved or dispersed in ethanol or purified water to prepare a second coating solution. This coating solution is sprayed onto the above-obtained granules, which are then dried to obtain enteric granules.

Optionally, one or more intermediate layers containing a non-water-soluble polymer, a water-decomposable or water-dispersible substance, a water-soluble polymer or a lubricant may also be formed between the first coating layer and the second coating layer.

Examples of the means for spraying the above-described coating solution include a centrifugal fluid granulator/coater, a fluid bed granulator/coater and a Wurster-type fluid bed granulator/coater.

EXAMPLES

The present invention will now be described in more detail with reference to the following Examples. However, the present invention is not limited to these Examples.

Production Examples

2-[[[4-(2,2-dimethyl-1,3-dioxan-5-yl)methoxy-3,5-dimethylpyridin-2-yl]methyl]sulfinyl]-1H-benzimidazole sodium salt (1) 2,3,5-trimethylpyridine 1-oxide

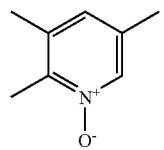

[Formula 1]

2,3,5-trimethylpyridine (1.43 kg, 11.80 mol) was charged over 15 minutes into acetic acid (1.43 kg, 23.83 mol). After 15 minutes, 35% hydrogen peroxide water (1.38 kg, 14.2 mol) was added dropwise into the solution over 30 minutes. The resultant solution was then stirred overnight at 90 to 95° C. The reaction solution was charged with sodium sulfite (220 g). This reaction mixed solution was charged with sodium carbonate (2.5 kg) and water (12 L), and the resultant mixture was extracted with chloroform (3.0 L×4). The resultant organic layer was concentrated until crystals precipitated. The precipitate was charged with n-hexane (2.5 L), and the solution was stirred overnight under ice cooling. The obtained crystals were filtered to obtain 1.53 kg of the title compound.

(2) 2,3,5-trimethyl-4-nitropyridine 1-oxide

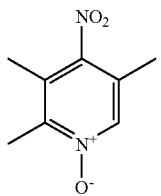

[Formula 2]

2,3,5-trimethylpyridine 1-oxide (1.38 kg, 10.1 mol) was charged into 98% sulfuric acid (4.93 kg, 49.3 mol). 97% nitric acid (1.44 kg) was added dropwise to the solution over 50 minutes, and the solution was then heated for 4 hours at 85° C. The reaction solution was charged into a mixture of ammonium hydrogencarbonate (10.6 kg) and water (9.0 L), and the resultant mixture was extracted with ethyl acetate (3.0 L×3). The resultant organic layer was concentrated and then dried overnight under vacuum to obtain 1.50 kg of the title compound.

(3) 4-Chloro-2,3,5-trimethylpyridine 1-oxide

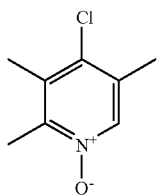

[Formula 3]

2,3,5-trimethyl-4-nitropyridine 1-oxide (850 g, 4.67 mol) was charged with water (400 g) and 36% concentrated hydrochloric acid (1.69 kg), and the resultant solution was heated to 70° C. The solution was then charged with N,N-dimethylformamide (115 mL) and heated to 100° C. Once the reaction had finished, the solution was cooled to 20° C. and then charged into a mixture of potassium carbonate (1.40 kg) and water (7 L). The resultant mixture was extracted with chloroform (1.0 L×3), dried over sodium sulfate and then concentrated. The resultant crude product was stirred for 2 hours in a mixed solution of diisopropyl ether (500 mL) and n-hexane (1.0 L), and the resultant solution was then filtered with suction. The resultant wet substance was dried overnight under vacuum to obtain 666.4 q of the title compound.

(4) 4-(2,2-dimethyl-1,3-dioxan-5-ylmethoxy)-2,3,5-trimethylpyridine 1-oxide

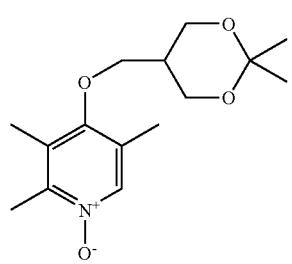

[Formula 4]

A mixture of 4-chloro-2,3,5-trimethylpyridine 1-oxide (840 g), (2,2-dimethyl-1,3-dioxan-5-yl)methanol (688 g) and toluene (2.52 L) was heated to reflux while removing moisture. While continuing the azeotropic dewatering, the mixture was charged with potassium hydroxide (0.58 kg) over 3 hours and 45 minutes, and the azeotropic dewatering was then continued for another 2.5 hours. The reaction system was cooled to 30° C. or less and then charged with ethyl acetate (2.5 L) and 17% saline solution (3.5 L). The resultant solution was left to stand overnight. The ethyl acetate layer was collected, and the aqueous layer was extracted with ethyl acetate (1.0 L×3). The combined ethyl acetate layers were filtered with Celite and then concentrated under reduced pressure to obtain 1.20 kg of the title compound.

(5) [4-(2,2-dimethyl-1,3-dioxan-5-yl)methoxy-3,5-dimethylpyridin-2-yl]methanol monohydrate

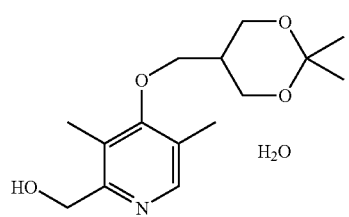

[Formula 5]

Acetic anhydride (1.10 kg) was added dropwise over 1.5 hours to a mixture heated to 50 to 60° C. of 4-(2,2-dimethyl-1,3-dioxan-5-yl)methoxy-2,3,5-trimethylpyridine 1-oxide (1.20 kg) and sodium acetate (0.18 kg). After 0.5 hours had passed, the mixture was heated for 4.5 hours at 80° C. The mixture was then cooled so that its internal temperature was not greater than 30° C., and left to stand. The mixture was then concentrated under reduced pressure. The resulting residue was dissolved in methanol (1.0 L), and the resultant solution was then charged over 1 hour into a mixture of 48% aqueous sodium hydroxide (0.71 kg) and chilled water (2.85 L). The solution was stirred at room temperature for 5 hours and 45 minutes, and then concentrated under reduced pressure. The concentrated residue was charged with water (3.0 L), and the resultant mixture was extracted with toluene (2.3 L×4). The combined toluene layers were washed with water (1.2 L). The resultant organic layer was filtered with Celite and then concentrated. The resulting residue was charged with diisopropyl ether (1.15 L) at room temperature, and this solution was further charged with warm water (45° C., 74 mL). Once crystal precipitation had been confirmed, the solution was stirred for 1 hour at 25° C. and then charged with heptane (3.6 L). The stirring was continued overnight. After stirring for a further 5 hours under ice cooling, the solution was filtered to obtain yellow crystals. The obtained yellow crystals were charged with diisopropyl ether (3.5 L) and dissolved at 50° C. Insoluble matter was removed by filtration, and the solution was then slowly cooled and allowed to age overnight at 5° C. The obtained crystals were filtered, washed with heptane (0.5 L) and wind-dried to obtain 0.69 kg of the title compound.

(6) 2-[[[4-(2,2-dimethyl-1,3-dioxan-5-yl)methoxy-3,5-dimethylpyridin-2-yl]methyl]thio]-1H-benzimidazole

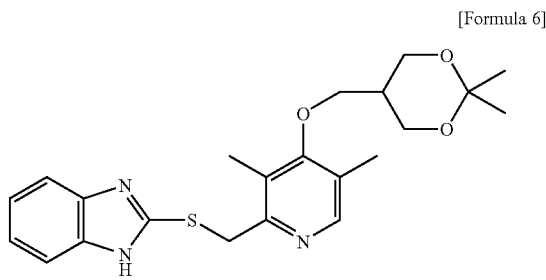 [SMILES: Cc1cnc(CSc2nc3ccccc3[nH]2)c(C)c1OCC1COC(C)(C)OC1]

[Formula 6]

Toluene was charged into [4-(2,2-dimethyl-1,3-dioxan-5-yl)methoxy-3,5-dimethylpyridin-2-yl]methanol monohydrate (690 g) and azeotropic dewatering was carried out (2.1 L×5, 1.75 L×1). The resultant concentrated product was charged with toluene (393 mL) to obtain 921 g of a solution of [4-(2,2-dimethyl-1,3-dioxan-5-yl)methoxy-3,5-dimethylpyridin-2-yl]methanol in toluene.

Under a nitrogen atmosphere, a solution of [4-(2,2-dimethyl-1,3-dioxan-5-yl)methoxy-3,5-dimethylpyridin-2-yl]methanol in toluene (845.7 g, content percentage 61.7%, content amount 521.8 g, 1.855 mol), tetrahydrofuran (2,609 mL), toluene (669 mL) and triethylamine (375.3 g, 3.709 mol) were successively charged together, and the resultant solution was stirred while cooling with dry ice/ethanol. From 30 minutes after the start of cooling, methanesulfonyl chloride (254.9 g, 2.226 mol) was added dropwise to the solution over 42 minutes. Once the dropping had finished, the solution was stirred while cooling with an ice bath. After about 1.5 hours, the solution was charged over 2 minutes with a solution of 2-mercaptobenzimidazole (334.28 g, 2.226 mol) in tetrahydrofuran (3,653 mL), and stirring was continued at room temperature for about 18 hours.

The reaction solution was charged with toluene (3,653 mL) and then charged with 20% w/w aqueous sodium hydroxide (1,852.4 g). The resultant solution was further charged with $H_2O$ (2,322 mL) and the mixture was extracted and separated. The organic layer was washed twice with 20% w/w aqueous ammonium chloride and then further washed with $H_2O$ (4,147 mL).

The resultant organic layer was concentrated under reduced pressure (40° C.) to obtain a brown, oily substance (2.40 kg, containing 1,446 mL of toluene and 168 mL of tetrahydrofuran as calculated from the $^1$H-NMR spectrum).

The obtained brown, oily substance was moved to a crystallization vessel, washed with toluene (119 mL) and then stirred at room temperature. After 10 minutes, the solution was charged with tert-butylmethyl ether (134 mL) and the stirring was continued at room temperature. After 20 minutes, the solution was charged with more tert-butylmethyl ether (127 mL) and the stirring was continued at room temperature. After 30 minutes, more tert-butylmethyl ether (266 mL) was added dropwise over 20 minutes to the solution, and the stirring was continued at room temperature. One minute later, more tert-butylmethyl ether (522 mL) was added dropwise to the solution. Eight minutes later crystal precipitation was confirmed. The dropping was finished after taking a total of 1 hour and 20 minutes.

Stirring was carried out at room temperature for another 40 minutes, after which heptane was added dropwise to the solution over 1 hour 17 minutes. The solution was then stirred at room temperature overnight.

Heptane was added dropwise for about 15.5 hours. The precipitated crystals were then filtered off with suction, rinsed with toluene/tert-butylmethyl ether/heptane (587 mL/391 mL/587 mL) and then dried by suction. The resultant wet crystals were blow-dried (50° C.) to obtain the title compound.

Yield amount: 619.0 g; content percentage: 96.5%;
content amount: 597.3 g; yield percentage: 77.8% (content amount base); HPLC purity: 98.0%<

HPLC analysis conditions (Reaction check, HPLC purity check, and quantitative)>
Column: YMC-Pack Pro C18 AS-302 (5 μm, 4.6 mm×150 mm I.D.)
Eluent: A solution (MeCN/20 mM AcONH4 aq.=100/900 (v/v)), B solution (MeCN/20 mM AcONH4 aq.=800/200 (v/v))
Flow rate: 1.0 mL/min
Detection: UV 254 nm
Oven temp.: 25° C.
Sample temp.: 25° C.
Gradient condition (time/B solution conc.): 0.01 min/0%→25 min/100%→30 min/100%→30.01 min/0%→40 min/stop
RT=18.4 min

(7) Crude 2-[[[4-(2,2-dimethyl-1,3-dioxan-5-yl)methoxy-3,5-dimethylpyridin-2-yl]methyl]sulfinyl]-1H-benzimidazole sodium salt

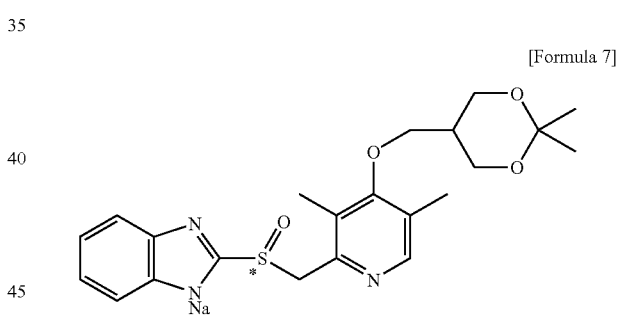

[Formula 7]

The moisture content in the 2-[[[4-(2,2-dimethyl-1,3-dioxan-5-yl)methoxy-3,5-dimethylpyridin-2-yl]methyl]thio]-1H-benzimidazole, toluene, L-(+)-diethyl tartrate and N,N-diisopropylethylamine to be used in the reaction was measured by the Karl Fischer method (total amount: 0.885 g).

Under a nitrogen atmosphere, 2-[[[4-(2,2-dimethyl-1,3-dioxan-5-yl)methoxy-3,5-dimethylpyridin-2-yl]methyl]thio]-1H-benzimidazole (580.3 g, content percentage: 96.5%, content amount: 560.0 g, 1.354 mol), toluene (3,864 mL) and $H_2O$ (2.81 g, 0.156 mol) were successively charged together, and the resultant solution was stirred under heating at 60° C. After 6 minutes, L-(+)-diethyl tartrate (122.9 g, 0.596 mol) was charged into the suspension, and the resultant solution was washed with toluene (560 mL). After 30 minutes, dissolution was confirmed. Eight minutes later, titanium(IV) tetraisopropoxide (77.0 g, 0.271 mol) was charged into the solution. The solution was then washed with toluene (56 mL) and stirred under heating at the same temperature for 1 hour.

The solution was cooled to 8° C., charged with N,N-diisopropylethylamine (56.01 g, 0.742 mol) and then washed with toluene (280 mL). After 10 minutes, a solution of cumene hydroperoxide (259.2 g, 1.422 mol) in toluene (840 mL) was added dropwise over 47 minutes, and the resultant solution was stirred at 8° C. for about 18.5 hours. The solution was charged with cooled 30% w/w aqueous sodium thiosulfate (2,240 g) and then stirred for 12 minutes. The aqueous layer was discarded, and the organic layer was charged with 4% w/w aqueous sodium hydroxide (2,240 g), stirred and then left to stand. The aqueous layer was then collected to obtain a 2-[[[4-(2,2-dimethyl-1,3-dioxan-5-yl)methoxy-3,5-dimethylpyridin-2-yl]methyl]sulfinyl]-1H-benzimidazole sodium hydroxide water extract as a yellow-brown suspension. The 2-[[[4-(2,2-dimethyl-1,3-dioxan-5-yl)methoxy-3,5-dimethylpyridin-2-yl]methyl]sulfinyl]-1H-benzimidazole sodium hydroxide water extract (2.98 kg) was charged into toluene (7,840 mL), and the resultant solution was stirred. This mixture was successively charged under stirring with 20% w/w aqueous acetic acid (400 mL), 8% aqueous NaOH (50 mL) and 20% w/w aqueous acetic acid (8 mL) to adjust the pH of the solution to 8.64. The solution was left to stand to separate the liquids, and the aqueous layer was discarded. The organic layer was washed with 5% w/w saline solution (2,240 g), and the liquids separated to obtain an extract of 2-[[[4-(2,2-dimethyl-1,3-dioxan-5-yl)methoxy-3,5-dimethylpyridin-2-yl]methyl]sulfinyl]-1H-benzimidazole in toluene (7.31 kg, 2-[[[4-(2,2-dimethyl-1,3-dioxan-5-yl)methoxy-3,5-dimethylpyridin-2-yl]methyl]sulfinyl]-1H-benzimidazole (content amount of 567.7 g, 1.322 mol)) as a yellow-brown solution.

The obtained toluene extract was charged over 1 minute with a solution of 28.3% sodium methoxide in methanol (245.6 g, 1.286 mol) while stirring at room temperature. Then, tert-butylmethyl ether (1,120 mL) was added dropwise over 3 minutes to this solution, and the resultant solution was stirred at room temperature. After 6 minutes, crystal precipitation was confirmed, and stirring was continued as is for about 30 minutes. Tert-butylmethyl ether (7,840 mL) was added dropwise for another 2 hours and 40 minutes, and the stirring was continued at room temperature overnight.

After adding dropwise tert-butylmethyl ether for about 13 hours, the precipitated crystals were filtered off with suction, rinsed with toluene/tert-butylmethyl ether (1,047 mL/1,193 mL) and then dried by suction for 15 minutes. The resultant wet crystals were dried (40° C.) under reduced pressure to obtain the title compound.
Yield amount: 546.8 g; content percentage: 101.7%;
content amount: 546.8 g (assuming 100% content percentage); yield percentage: 90.9% (content amount base); HPLC purity: 98.2%; enantiomeric excess: 100% ee
<HPLC Analysis Conditions (Reaction Check, HPLC Purity Check, and Quantitative)>
Column: YMC-Pack Pro C18 AS-302 (5 μm, 4.6 mm×150 mm I.D.)
Eluent: A solution (MeCN/20 mM AcONH4 aq.=100/900 (v/v)), B solution (MeCN/20 mM AcONH4 aq.=800/200 (v/v))
Flow rate: 1.0 mL/min
Detection: UV 254 nm
Oven temp.: 25° C.
Sample temp.: 25° C.
Gradient condition (time/B solution conc.): 0.01 min/0%→25 min/100%→30 min/100%→30.01 min/0%→40 min/stop
RT=14.1 min
<HPLC Analysis Conditions (Enantiomeric Excess)>
Column: Daicel Chiralpak IA (4.6 mm×250 mm I.D.)
Eluent: EtOH/MTBE=150/800 (v/v))
Flow rate: 1.0 mL/min
Detection: UV 284 nm
Oven temp.: 25° C.
Sample temp.: 25° C.

(8) Purified of 2-[[[4-(2,2-dimethyl-1,3-dioxan-5-yl) methoxy-3,5-dimethylpyridin-2-yl]methyl]sulfinyl]-1H-benzimidazole sodium salt

[Formula 8]

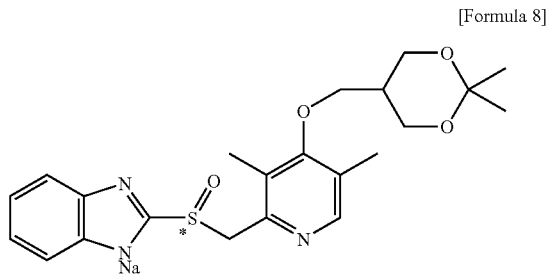

Crude sodium 2-[[[4-(2,2-dimethyl-1,3-dioxan-5-yl) methoxy-3,5-dimethylpyridin-2-yl]methyl]sulfinyl]-1H-benzimidazole (536.8 g, 1189 mol) was charged with ethanol (1,074 mL). The resultant mixture was dissolved at room temperature, and was then further charged with tert-butylmethyl ether (1,074 mL). This solution was filtered with suction using a Hyflo Super-Cel bed (107.4 g, product of successive washing with ethanol/tert-butylmethyl ether (1,074 mL/1, 074 mL) and tert-butylmethyl ether (537 mL)), and then rinsed with ethanol/tert-butylmethyl ether (215 mL/215 mL).

The obtained filtrate was moved to a crystallization vessel, washed with ethanol/tert-butylmethyl ether (54 mL/54 mL) and then stirred at room temperature. Tert-butylmethyl ether (1,610 mL) was added dropwise for 6 minutes and the stirring was continued at room temperature. After 11 minutes, tert-butylmethyl ether (268 mL) was added dropwise for 2 minutes and the stirring was continued. One minute later, crystal precipitation was confirmed, and stirring was continued at room temperature as is for 31 minutes. Tert-butylmethyl ether (268 mL) was then added dropwise for 9 minutes. After stirring at room temperature for 8 minutes, more tert-butylmethyl ether (8,589 mL) was added dropwise over a further 1 hour and 10 minutes. Stirring was continued at room temperature.

About 22 hours after tert-butylmethyl ether had finished being added dropwise, the precipitated crystals were collected by filtration while bubbling with nitrogen. The crystals were then successively washed with ethanol/tert-butylmethyl ether (107 mL/966 mL) and tert-butylmethyl ether (1,074 mL), and dried with suction for 8 minutes. Of the resultant wet crystals (584.54 g), 531.10 g were dried (50° C.) under reduced pressure to obtain the title compound.
Yield amount: 419.6 g; HPLC purity: 99.4%<
<HPLC Analysis Conditions (HPLC Purity Check and Quantitative)>
Column: YMC-Pack Pro C18 AS-302 (5 μm, 4.6 mm×150 mm I.D.)
Eluent: A solution (MeCN/20 mM AcONH4 aq.=100/900 (v/v)), B solution (MeCN/20 mM AcONH4 aq.=800/200 (v/v))
Flow rate: 1.0 mL/min
Detection: UV 254 nm
Oven temp.: 25° C.
Sample temp.: 25° C.

Gradient condition (time/B solution conc.): 0.01 min/0%→25 min/100%→30 min/100%→30.01 min/0%→40 min/stop
RT=14.1 min

Example 1

Granules (1)

160 g of sodium rabeprazole and 40 g of ethyl cellulose (Trade name: Ethocel, The Dow Chemical Company) were dissolved in 1,800 g of anhydrous ethanol. This solution was coated onto 800 g of the core substance Nonpareil 103 (Trade name, Freund Corporation) using a Wurster-type fluid bed granulator/coater (Trade name: Multiplex, Powrex Corporation). The coated cores were then dried to obtain granules.

Next, 137.6 g of ethyl cellulose (Trade name: Ethocel, The Dow Chemical Company) and 235 g of hydroxypropyl cellulose (Trade name: HPC-L, Shin-Etsu Chemical Co., Ltd.) were dissolved in 6,944.2 g of anhydrous ethanol, and 110.3 g of magnesium stearate (Mallinckrodt Inc.) was dispersed into the resultant solution. The solution was coated onto 800 g of the above-described granules, which were then dried to obtain intermediate-layer-coated granules.

Next, 336.8 g of hydroxypropylmethyl cellulose phthalate (Trade name: HP-55S, Shin-Etsu Chemical Co., Ltd.) and 33.7 g of diacetyl monoglyceride (Myvacet, Quest International) were dissolved in 8,083.2 g of 80% aqueous ethanol, and 49.5 g of blending pigment (Trade name: PB-44044, Colorcon, Inc.) was dispersed into the resultant solution. The solution was then coated onto 800 g of the above-described intermediate-layer-coated granules, which were then dried to obtain enteric granules.

The average particle size of these granules was measured using a sieve method to be 530 μm. The sieving was conducted using 850, 710, 600, 500 and 355 meshes, and passing the granules through 6 stages. The average particle size was calculated according to the weight ratio that passed through each of the mesh sections that the granules passed through.

Example 2

Granules (2)

362.8 g of sodium rabeprazole and 64.8 g of ethyl cellulose were dissolved in 3,848.6 g of anhydrous ethanol. This solution was coated onto 603.2 g of the core substance Nonpareil 108 using a Wurster-type fluid bed granulator/coater (Trade name: Multiplex, Powrex Corporation). The coated cores were then dried to obtain granules.

Next, 56.5 g of ethyl cellulose and 346.5 g of hydroxypropyl cellulose were dissolved in 8,132.7 g of anhydrous ethanol, and 162.4 g of magnesium stearate was dispersed into the resultant solution. The solution was coated onto 833.2 g of the above-described granules, which were then dried to obtain intermediate-layer-coated granules.

Further, 111.1 g of hydroxypropyl cellulose were dissolved in 2,500 g of anhydrous ethanol. 166.7 g of crospovidone (Trade name: Crospovidone XL-10, ISP Japan Ltd.) was dispersed into the solution. The resultant coating solution was coated onto 520.6 g of the above-described granules, which were then dried to obtain intermediate-layer-coated granules (granules having 2 intermediate layers).

Next, 214.2 g of hydroxypropylmethyl cellulose phthalate and 21.4 g of diacetyl monoglyceride were dissolved in 5,141.4 g of anhydrous ethanol solution, and 31.5 g of blending pigment was dispersed into the resultant solution. The solution was then coated onto 534.6 g of the above-described two-layer, intermediate-layer-coated granules to obtain enteric granules.

Examples 3 to 5 and Comparative Example 1 and 2

Granules were produced with the formula shown in Table 1 (calculated from the drying loss after production and the yield) in the same manner as described above. Adhesion and agglomeration among the granules occurred during the coating stage of the principal ingredient layer in Comparative Example 2, which did not contain ethyl cellulose in the same layer as the sodium rabeprazole.

TABLE 1

| Component | Comparative Example 1 | Comparative Example 2 | Example 3 | Example 4 | Example 5 |
|---|---|---|---|---|---|
| Nonpareil 108 | — | 33.3 | — | 16.8 | 16.8 |
| Nonpareil 103 | 128.1 | — | 58.0 | — | — |
| Crospovidone | 26.4 | — | — | — | — |
| HPC-L | 17.6 | — | — | — | — |
| Sodium rabeprazole | 10.0 | 10.0 | 10.0 | 10.0 | 10.0 |
| NaOH | 2.5 | — | — | — | — |
| Ethyl cellulose | — | — | 2.5 | 1.8 | 1.8 |
| Ethyl cellulose | 32.9 | — | 14.2 | 2.0 | 2.0 |
| HPC-L | 55.9 | — | 24.3 | 12.4 | 12.4 |
| Magnesium Stearate | 26.0 | — | 11.4 | 5.8 | 5.8 |
| Crospovidone XL-10 | — | — | — | — | 24.4 |
| HPC-L | — | — | — | — | 16.2 |
| HP-55S | 140.9 | — | 54.4 | 20.9 | 38.3 |
| Myvacet | 14.1 | — | 5.4 | 2.1 | 3.8 |
| PB-44044 | 20.7 | — | 8.0 | 3.1 | 5.6 |

Unit: g

Example 6

Drug Product Formulation (1) for Tube Administration

Sodium-rabeprazole-containing granules produced according to the method of Example 1 and placebo granules produced according to the following method were mixed in a weight ratio of 1:6.7 to obtain a drug product formulation for tube administration.

<Placebo Granule Production Method>

1,401.5 g of mannitol (Trade name: D-Mannitol, Towa Chemical Industry Co., Ltd.) and 1.5 g of ferric oxide red (Nihon Bengara Kogyo Co., Ltd.) were stirred using a high-speed stirring granulator (Trade name: Supermixer, Kawata Mfg., Co., Ltd.). The mixture was charged with 7.0 g of citric acid dissolved in 8.8 g of purified water, and the resultant solution was dried at 60° C. for 12 hours. The resultant product was then passed through a 20-mesh sieve to obtain a powder.

130.0 g of polyethylene glycol 8000 (NOF Corporation) and 160.0 g of propylene glycol alginate ester were charged into the above powder. The resultant mixture was stirred, and then using a high-speed stirring granulator (Trade name: Supermixer, Kawata Mfg., Co., Ltd.), granulated with anhydrous ethanol to produce granules. The granules were dried at 50° C. for 12 hours, and then passed through a 20-mesh sieve. 200.0 g of low-substituted hydroxypropyl cellulose (Trade name: L-HPC, Shin-Etsu Chemical Co., Ltd.), 60.0 g of aspartame (Ajinomoto Co., Inc.) and 40.0 g of strawberry flavor (Firmenich S.A.) were charged thereto, and the resultant mixture was thoroughly mixed using a high-speed stirrer to produce placebo granules which were free from any drugs.

Example 7

Drug Product Formulation (2) for Tube Administration

Sodium-rabeprazole-containing granules produced according to the method of Example 1 and placebo granules produced according to the following method were mixed in a weight ratio of 1:6.7 to obtain a preparation for tube administration.
<Placebo Granule Production>
Placebo granules were produced in the same manner as described above, with the formula shown in Table 2, except that propylene glycol alginate ester was changed to methyl cellulose.

TABLE 2

| Component | Placebo granules |
| --- | --- |
| Mannitol | 1341.5 |
| Ferric oxide Red | 1.5 |
| Citric acid | 7.0 |
| Polyethylene glycol 8000 | 130.0 |
| Methyl cellulose | 220.0 |
| Low-substituted hydroxylpropyl cellulose | 200.0 |
| Aspartame | 60.0 |
| Strawberry flavor | 40.0 |

Unit: g

Example 8

Tablets 6 g of granule formulation produced according to the method of Example 1 was charged with 4 g of mannitol (Roquette Freres), 4 g of crystalline cellulose (Avicel 102, Asahi Kasei Corporation), 0.5 g of low-substituted hydroxypropyl cellulose (Trade names: L-HPC, LH-21, Shin-Etsu Chemical Co., Ltd.), 0.1 g of aspartame (Ajinomoto Co., Inc.), 0.014 g of menthol corn (Takasago International Corporation) and 0.04 g of sodium stearyl fumarate (Penwest Pharmaceuticals Co.), and the resultant mixture was thoroughly mixed. The mixture was subjected to pressure-molding using an Autograph (Trade name: AG-5000A, Shimadzu Corporation) to obtain 13-mm-diameter tablets containing 600 mg per tablet.

Example 9

Encapsulated Formulation

The granule formulation produced according to the method of Example 5 was filled into hard capsules using a hand-filling capsule filling machine (Trade name: ProFill Capsule Filling System, Capsugel Japan Inc.) to contain 130 mg per capsule to obtain encapsulated formulations.

Test Examples

Test Example 1

Dissolution Test

The granule formulations produced according to the methods of Comparative Example 1 and Examples 3 and 4 were subjected to a dissolution test (method as described in the Japanese Pharmacopoeia) by a paddle method using a tris-HCl buffer solution adjusted to a pH of 8.0. The sampling solutions were measured by HPLC, and the dissolution rate of rabeprazole was calculated. The results are shown in FIG. 1.

From the results of the dissolution test, it is clear that the tablets according to the present invention are an excellent drug product formulation which dissolves 75% or more of the rabeprazole within 30 minutes.

Test Example 2

Stability Test

The granule formulations produced according to the methods of Examples 3 to 5 and Comparative Example 1 were placed in a hygroscopic aluminum sachet or a No. 2 bottle (containing silica gel) made from polyester resin, and then stored under the conditions shown in Table 3. The granules were dissolved using an acetonitrile/borate buffer solution having a pH of 11.0, and then subjected to centrifugal separation. The supernatant was analyzed by HPLC, and the amount of formed decomposed matter was measured.

TABLE 3-1

| Storage conditions | Comparative Example 1 Aluminum sachet | Example 3 Aluminum sachet |
| --- | --- | --- |
| Initial | 1.17% | 0.41% |
| 25° C., one-month storage | 1.28% | 0.54% |
| 40° C., one-month storage | 2.00% | 0.85% |

TABLE 3-2

| Storage conditions | Example 4 Polyester bottle | Example 5 Polyester bottle |
| --- | --- | --- |
| Initial | 0.55% | 0.56% |
| 25° C., one-month storage | 0.66% | 0.55% |
| 40° C., one-month storage | 0.66% | 0.73% |

From the above results, it can be seen that the amount of decomposed matter after storage for the granule formulation of Example 3, in which ethyl cellulose was blended in the same coating layer as the sodium rabeprazole, was clearly less than that for the non-blended Comparative Example 1. Further, the occurrence of decomposed matter in Examples 4 and 5, in which the storage mode was changed to a bottle made from polyester resin, was about as low as that for an aluminum sachet.

Test Example 3

Stability Test

The granule formulations produced according to the methods of Examples 4 and 5 were placed in a No. 2 bottle (not containing silica gel) made from polyester resin and stored under the conditions shown in Table 4. The rabeprazole in the granules was then dissolved using an acetonitrile/borate buffer solution having a pH of 11.0, and subjected to centrifugal separation. The supernatant was analyzed by HPLC, and the amount of formed decomposed matter was measured.

TABLE 4

| Storage conditions | Example 4 | Example 5 |
|---|---|---|
| 5° C., one-month storage | 0.55% | 0.55% |
| 25° C., one-month storage | 0.63% | 0.56% |
| 40° C., one-month storage | 1.46% | 0.95% |

From the above results, it is clear that the occurrence of decomposed matter was low for all of the granules and that the drug product formulations are excellent pharmaceutical compositions which are not easily effected by moisture in the external air.
Further, the occurrence of decomposed matter when stored at 40° C. was even lower for the granule formulation of Example 5, which was provided with an intermediate layer containing crospovidone.

Example 10

Encapsulated Formulation 30.0 g of 2-[[[4-(2,2-dimethyl-1,3-dioxan-5-yl)methoxy-3,5-dimethylpyridin-2-yl]methyl]sulfinyl]-1H-benzimidazole sodium salt (hereinafter, "compound A"), 8.1 g of ethyl cellulose (Trade name: Ethocel, The Dow Chemical Company) and 16.2 g of hydroxypropyl cellulose (Trade name: HPC-L, Shin-Etsu Chemical Co., Ltd.) were dissolved in 489 g of anhydrous ethanol. This solution was coated onto 500.1 g of the core substance Nonpareil 108 (Trade name, Freund Corporation) using a Wurster-type fluid bed granulator/coater (Trade name: Multiplex, Powrex Corporation). The coated cores were then dried to obtain granules.

Next, 48.6 g of ethyl cellulose (Trade name: Ethocel, The Dow Chemical Company) and 291.9 g of hydroxypropyl cellulose (Trade name: HPC-L, Shin-Etsu Chemical Co., Ltd.) were dissolved in 6,860 g of anhydrous ethanol, and 136.8 g of magnesium stearate (Mallinckrodt Inc.) was dispersed into the resultant solution. The solution was coated onto 554.4 g of the above-described granules, which were then dried to obtain intermediate-layer-coated granules.

Next, 460.2 g of hydroxypropylmethyl cellulose phthalate (Trade name: HP-55S, Shin-Etsu Chemical Co., Ltd.) and 45.3 g of diacetyl monoglyceride (Trade name: Myvacet, Quest International) were dissolved in 11,045 g of 80% aqueous ethanol, and 42.3 g of talc (Trade name: Talc, Matsumura Sangyo Co., Ltd.) and 24.3 g of titanium oxide (Trade name: Titanium(IV) Oxide, Merck Ltd.) were dispersed into the resultant solution. The solution was then coated onto 1,031.7 g of the above-described intermediate-layer-coated granules, which were then dried to obtain enteric granules.

15.0 g of light anhydrous silicic acid (Trade name: Japanese Pharmacopoeia Aerosil-200, Nippon Aerosil Co., Ltd.) and 15.0 g of talc (Trade name: Hi-filler #17, Matsumura Sangyo Co., Ltd.) were charged into 1,603.8 g of the above-described enteric granules. The resultant mixture was mixed using a vessel-type mixer (Trade name: 2/5 L Vessel-type Mixer, Toyo Packing Co., Ltd.), and then filled into capsules as compound A so that 1 mg was filled per capsule.

Example 11

Encapsulated Formulation

Granules were produced according to the following formula in the same manner as in Example 10. The granules were filled into capsules as compound A so that 10 mg was filled per capsule.

TABLE 5

| Component | Example 11 |
|---|---|
| Nonpareil 108 | 465.0 |
| Principal ingredient layer | |
| Compound A | 500.0 |
| Ethyl cellulose | 135.0 |
| HPC-L | 270.0 |
| Intermediate layer | |
| Ethyl cellulose | 40.0 |
| HPC-L | 240.0 |
| Magnesium stearate | 112.5 |
| Exterior layer | |
| HP-55S | 380.0 |
| Myvacet | 37.5 |
| Talc | 35.0 |
| Titanium oxide | 20.0 |
| AEROSIL-200 | 30.0 |
| Talc | 30.0 |

Unit: g

Examples 12 to 14

Encapsulated Formulation

Granules were produced according to the following formula in the same manner as in Example 1. The granules were filled into capsules as sodium rabeprazole so that 10 mg was filled per capsule.

TABLE 6

| Component | Example 12 | Example 13 | Example 14 |
|---|---|---|---|
| Nonpareil 108 | 16.7 | 16.7 | 16.7 |
| Principal ingredient layer | | | |
| Sodium rabeprazole | 10.0 | 10.0 | 10.0 |
| Ethyl cellulose | 1.8 | 1.8 | 1.8 |
| Magnesium oxide | 1.1 | 3.3 | 10.0 |
| Intermediate layer | | | |
| Ethyl cellulose | 5.1 | 5.5 | 6.7 |
| HPC-L | 31.3 | 33.7 | 40.8 |
| Magnesium Stearate | 14.7 | 15.8 | 19.1 |
| Exterior layer | | | |
| HP-55S | 91.4 | 98.3 | 118.9 |
| Myvacet | 9.1 | 9.8 | 11.9 |
| Talc | 4.8 | 5.2 | 6.3 |

TABLE 6-continued

| Component | Example 12 | Example 13 | Example 14 |
|---|---|---|---|
| Titanium oxide | 8.4 | 9.0 | 10.9 |
| Aerosil-200 | 1.0 | 1.0 | 1.3 |
| Talc | 1.0 | 1.0 | 1.3 |

Unit: mg

Examples 15 to 16

Encapsulated Formulation

Granules were produced according to the following formula in the same manner as in Example 10. The granules were filled into capsules s compound A so that 10 mg was filled per capsule.

TABLE 7

| Component | Example 15 | Example 16 |
|---|---|---|
| Nonpareil 108 | 9.7 | 23.4 |
| Principal ingredient layer | | |
| Compound A | 40.0 | 40.0 |
| Ethyl cellulose | 10.8 | 10.8 |
| Magnesium oxide | 13.3 | 13.3 |
| HPC-L | 21.6 | 21.6 |
| Intermediate layer | | |
| Ethyl cellulose | 3.3 | 5.0 |
| HPC-L | 19.9 | 30.1 |
| Magnesium Stearate | 9.3 | 14.1 |
| Exterior layer | | |
| Eudragit L30D-55 | 45.8 | — |
| Triethyl citrate | 4.6 | — |
| HP-55S | — | 47.8 |
| Myvacet | — | 4.7 |
| Talc | 23.0 | 4.4 |
| Titanium oxide | — | 2.5 |
| Aerosil-200 | 2.0 | 2.2 |
| Talc | 2.0 | 2.2 |

Unit: mg

Test Example 4

Dissolution Test

Figure 2:
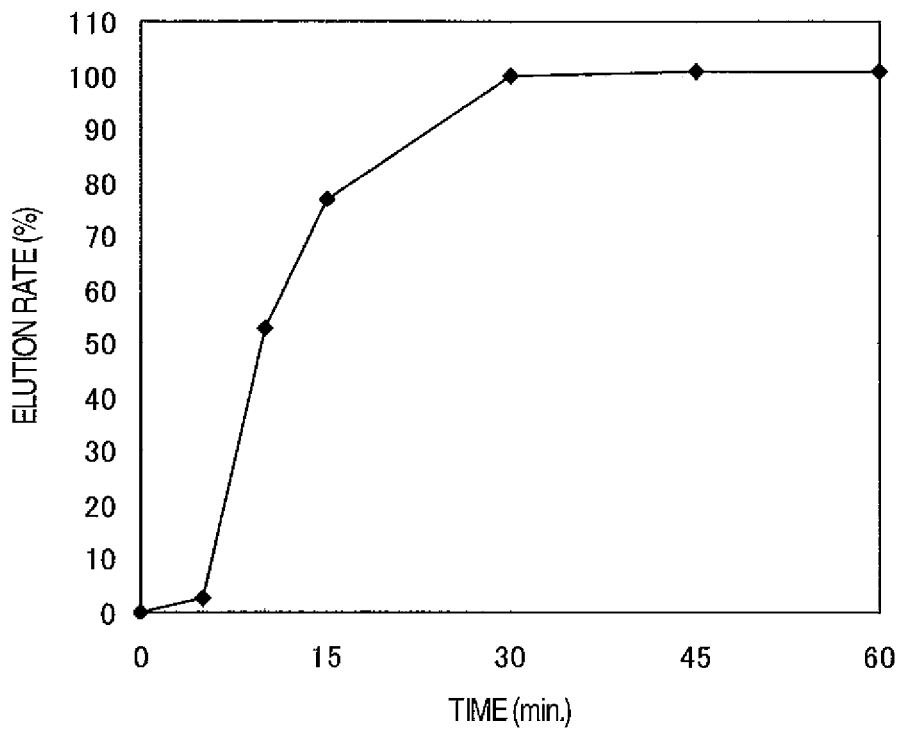
FIG. 2 is a graph showing the results of the dissolution test of the granule formulations according to the present invention.

The granule formulation produced according to the method of Example 10 was subjected to a dissolution test (method as described in the Japanese Pharmacopoeia) by a paddle method using a 50 mM phosphoric acid buffer solution adjusted to a pH of 6.8. The sampling solution was measured by HPLC, and the dissolution rate of compound A was calculated. The results are shown in FIG. 2.

From the results of the dissolution test, it is clear that the tablets according to the present invention are an excellent drug product formulation which dissolves almost 100% of the compound A within 30 minutes.

The invention claimed is:

1. A pharmaceutical composition comprising a core substance coated with a principal ingredient layer,
    said principal ingredient layer comprising rabeprazole or a pharmaceutically acceptable salt thereof as a proton pump inhibitor and ethyl cellulose; and
    said principal ingredient layer does not contain a basic substance.

2. The pharmaceutical composition according to claim 1, wherein the pharmaceutical composition is further coated with an exterior layer comprising an enteric polymer on an exterior side of the principal ingredient layer.

3. The pharmaceutical composition according to claim 2, wherein the enteric polymer is one or more selected from the group consisting of hydroxypropylmethyl cellulose phthalate, hydroxypropylmethyl cellulose acetate succinate, methacrylic acid methacrylic acid methyl copolymer, methacrylic acid acrylic acid ethyl copolymer, carboxymethylethyl cellulose and cellulose acetate phthalate.

4. The pharmaceutical composition according to claim 2, wherein one or more intermediate layers is coated between the principal ingredient layer and the exterior layer.

5. The pharmaceutical composition according to claim 4, wherein two intermediate layers are coated.

6. The pharmaceutical composition according to claim 4, wherein at least one of the intermediate layers comprises one or more selected from the group consisting of a non-water-soluble polymer, a water-soluble polymer and a lubricant.

7. The pharmaceutical composition according to claim 4, wherein the composition comprises two or more intermediate layers, and wherein at least one of the intermediate layers comprises a non-water-soluble polymer, a water-soluble polymer and a lubricant, and another intermediate layer comprises crospovidone.

8. The pharmaceutical composition according to claim 1, wherein based on the total amount of the layer comprising the rabeprazole or pharmaceutically acceptable salt thereof and ethyl cellulose, the weight of ethyl cellulose in said layer is not more than 25%.

9. The pharmaceutical composition according to claim 1, wherein the core substance is a granule substance having one or more components selected from the group consisting of sugars, sugar alcohols, celluloses and starches.

10. The pharmaceutical composition according to claim 1, which is a granule.

11. The pharmaceutical composition according to claim 1, which is a tablet or an encapsulated formulation.

12. The pharmaceutical composition according to claim 10, which is a drug product formulation used for tube administration further comprising a thickening agent.

13. The pharmaceutical composition according to claim 2, wherein in a dissolution test using a test solution having a pH of 5.5 or higher, 75% or more of the rabeprazole compound is dissolved within 30 minutes.

* * * * *